(12) United States Patent
Nakatani et al.

(10) Patent No.: US 9,284,608 B2
(45) Date of Patent: *Mar. 15, 2016

(54) SENSOR

(71) Applicant: Panasonic Intellectual Property Management Co., Ltd., Osaka (JP)

(72) Inventors: Masaya Nakatani, Osaka (JP); Makoto Takahashi, Osaka (JP); Hiroshi Ushio, Osaka (JP); Daniel Yazbeck, San Jose, CA (US)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 42 days.

This patent is subject to a terminal disclaimer.

(21) Appl. No.: 13/928,888

(22) Filed: Jun. 27, 2013

(65) Prior Publication Data

US 2013/0288350 A1    Oct. 31, 2013

Related U.S. Application Data

(62) Division of application No. 13/002,691, filed as application No. PCT/JP2009/002949 on Jun. 26, 2009, now Pat. No. 8,962,248.

(30) Foreign Application Priority Data

Jul. 9, 2008 (JP) ................................. 2008-178980
Jan. 14, 2009 (JP) ................................. 2009-005804

(51) Int. Cl.
*C12Q 1/68* (2006.01)
*B01J 19/00* (2006.01)

(52) U.S. Cl.
CPC ........... *C12Q 1/6876* (2013.01); *B01J 19/0046* (2013.01); *C12Q 1/6825* (2013.01);
(Continued)

(58) Field of Classification Search
CPC .. C12Q 1/6837; C12Q 1/6825; C12Q 1/6874; C12Q 1/6876; C12Q 2565/507; B01J 19/0046; B01J 2219/00432; B01J 2219/00509; B01J 2219/00529; B01J 2219/00585; B01J 2219/00596; B01J 2219/00608; B01J 2219/00612; B01J 2219/00635; B01J 2219/00637; B01J 2219/00644; B01J 2219/00659; B01J 2219/00722
See application file for complete search history.

(56) References Cited

U.S. PATENT DOCUMENTS 5,143,854 A    9/1992  Pirrung et al.
5,405,783 A    4/1995  Pirrung et al.
(Continued)

FOREIGN PATENT DOCUMENTS

EP    1 620 256    2/2006
EP    1 725 189    11/2006
(Continued)

OTHER PUBLICATIONS

International Search Report issued Sep. 29, 2009 in International (PCT) Application No. PCT/JP2009/002949.
(Continued)

*Primary Examiner* — Young J Kim
(74) *Attorney, Agent, or Firm* — Wenderoth, Lind & Ponack, L.L.P.

(57) ABSTRACT

A sequencer that measures a nucleic acid sequence in a nucleic acid strand includes: a base material having a surface made of silicon, and a fibrous protrusion that is made of silicon dioxide and is directly joined to the surface of the base material made of silicon, wherein a plurality of the nucleic acid strands are fixed onto the fibrous protrusion.

7 Claims, 10 Drawing Sheets

(52) U.S. Cl.
CPC ............ *C12Q1/6837* (2013.01); *C12Q 1/6874* (2013.01); *B01J 2219/00432* (2013.01); *B01J 2219/00509* (2013.01); *B01J 2219/00529* (2013.01); *B01J 2219/00585* (2013.01); *B01J 2219/00596* (2013.01); *B01J 2219/00608* (2013.01); *B01J 2219/00612* (2013.01); *B01J 2219/00635* (2013.01); *B01J 2219/00637* (2013.01); *B01J 2219/00644* (2013.01); *B01J 2219/00659* (2013.01); *B01J 2219/00722* (2013.01)

(56) References Cited

U.S. PATENT DOCUMENTS

| | | | |
|---|---|---|---|
| 6,627,842 | B1 | 9/2003 | Fonash et al. |
| 7,115,400 | B1 | 10/2006 | Adessi et al. |
| 8,557,195 | B2 * | 10/2013 | Nakatani et al. ............ 422/400 |
| 2003/0119034 | A1 | 6/2003 | Kang et al. |
| 2003/0152957 | A1 | 8/2003 | Shinohara et al. |
| 2004/0136866 | A1 | 7/2004 | Pontis et al. |
| 2005/0038498 | A1 | 2/2005 | Dubrow et al. |
| 2005/0221072 | A1 | 10/2005 | Dubrow et al. |
| 2006/0159916 | A1 | 7/2006 | Dubrow et al. |
| 2006/0204738 | A1 | 9/2006 | Dubrow et al. |
| 2007/0282247 | A1 | 12/2007 | Desai et al. |
| 2008/0014630 | A1 | 1/2008 | Furuki |
| 2009/0162643 | A1 | 6/2009 | Dubrow et al. |
| 2009/0236648 | A1 | 9/2009 | Maeda et al. |
| 2010/0004695 | A1 | 1/2010 | Stad et al. |
| 2010/0219488 | A1 | 9/2010 | Nakatani et al. |
| 2011/0111984 | A1 * | 5/2011 | Nakatani et al. ............ 506/16 |
| 2011/0232794 | A1 | 9/2011 | Nakatani et al. |

FOREIGN PATENT DOCUMENTS

| | | |
|---|---|---|
| EP | 2 172 415 | 4/2010 |
| JP | 4-505763 | 10/1992 |
| JP | 2005-525125 | 8/2002 |
| JP | 2003-315349 | 11/2003 |
| JP | 2003-322653 | 11/2003 |
| JP | 2006-45668 | 2/2006 |
| JP | 2007-526439 | 9/2007 |
| JP | 2007-279028 | 10/2007 |
| JP | 2007-285927 | 11/2007 |
| JP | 2007-533371 | 11/2007 |
| JP | 2008-020412 | 1/2008 |
| JP | 2010-183900 | 8/2010 |
| JP | 2010-208885 | 9/2010 |
| WO | 03/046508 | 6/2003 |
| WO | WO 03046508 A2 * | 6/2003 |
| WO | 2004/099068 | 11/2004 |
| WO | 2005/084582 | 9/2005 |
| WO | 2007/046432 | 4/2007 |
| WO | 2007/078304 | 7/2007 |
| WO | 2008/018834 | 2/2008 |
| WO | 2008/103464 | 8/2008 |
| WO | 2009/034697 | 3/2009 |
| WO | 2010/004695 | 1/2010 |
| WO | 2010/082279 | 7/2010 |

OTHER PUBLICATIONS

Written Opinion of the International Searching Authority issued Feb. 8, 2011 in International Application No. PCT/JP2009/002949.
Supplementary Europe Search Report issued Oct. 27, 2011 in European Patent Application No. 09 79 4143.
B. Ramana Murthy et al., "Silicon nanopillar substrates for enhancing signal intensity in DNA microarrays", Biosensors and Bioelectronics, vol. 24, No. 4, pp. 723-728, XP025535143, ISSN: 0956-5663, Jul. 6, 2008.
C. Oillic et al., "DNA microarrays on silicon nanostructures: Optimization of the multilayer stack for fluorescence detection", Biosensors and Bioelectronics, vol. 22, No. 9-10, pp. 2086-2092, SP 002661003, ISSN: 0956-5663, Apr. 2007.
Extended European Search Report issued Jun. 28, 2012 in corresponding European Application No. 09 794 143.9.
Hai Ni et al.; "Elastic Modulus of Amorphous $SiO_2$ Nanowires"; Applied Physics Letters; 2006; vol. 88, 043108; pp. 1-3.
Ki-Hong Lee, et al.; "Direct Growth of Amorphous Silica Nanowires by Solid State Transformation of $SiO_2$ films"; Chemical Physics Letters; 2004; vol. 383; pp. 380-384.
H. F. Yan, et al.; "Growth of Amorphous Silicon Nanowires Via a Solid-Liquid-Solid Mechanism"; Chemical Physics Letters; 2000; vol. 323; pp. 224-228.
European Search Report issued Oct. 15, 2013 in European Paent Application No. EP 13 17 3138.
Anton Ressine et al., "Macro-/Nanoporous Silicon as a Support for High-Performance Protein Microarrays", Analytical Chemistry, American Chemical Society, vol. 75, No. 24, XP001047371, ISSN: 0003-2700, pp. 6968-6974, Dec. 15, 2003.
Kerstin Jaras et al., "ENSAM: Europium Nanoparticles for Signal Enhancement of Antibody Microarrays on Nanoporous Silicon", Journal of Proteome Research, vol. 7, No. 3, XP002714121, ISSN: 1535-3893, pp. 1308-1304, Mar. 3, 2008.
Cornelia Steinhauer et al., "Biocompatibility of surfaces for antibody microarrays: design of macroporous silicon substrates", Analytical Biochemistry, Academic Press, Inc., vol. 341, No. 2, XP004901270, ISSN: 0003-2967, pp. 204-213, Jun. 15, 2005.
Official Communication from European Patent Office issued Jun. 17, 2014 in corresponding European Patent Application No. EP 13 173 138.2.
Alpa C. Patel et al., "In Situ Encapsulation of Horseradish Peroxidase in Electrospun Porous Silica Fibers for Potential Biosensor Applications", Nano Letters, vol. 6, No. 5, pp. 1042-1046, XP55122823, ISSN: 1530-6984, DOI: 10.1021/n10604560, May 1, 2006.
Japanese Office Action (OA) dated Mar. 18, 2014 in corresponding Japanese Patent Application No. 2009-156945.
S.Y. Huang et al., "Plasma-enabled growth of ultralong straight, helical, and branched silica photonic nanowires", Journal of Applied Physics, vol. 104, 033301, pp. 1-7, doi: 10.1063/1.2963694, Aug. 2008.
Scott J. Tebbutt, "Genotyping of Single Nucleotide Polymorphisms by Arrayed Primer Extension", Methods Mol. Biol., (2007), vol. 382, pp. 149-161.
Yen Wei et al., "A Novel Method for Enzyme Immobilization: Direct Encapsulation of Acid Phosphatase in Nanoporous Silica Host Materials", Journal of Nanoscience and Nanotechnology, American Scientific Publishers, U.S., vol. 1, No. 1, pp. 83-93, XP009053115, ISSN: 1533-4880, DOI: 10.1166/JNN.2001.014, Mar. 1, 2001.
Written Opinion of the International Searching Authority dated May 11, 2010 issued in International Patent Application No. PCT/JP2011/002566.

* cited by examiner

SENSOR

BACKGROUND

1. Technical Field

The present invention relates to a sequencer that measures a sequence of nucleic acids such as DNAs.

2. Background Art

As a conventional sensor, there is a DNA sensor, for example, as shown in FIG. 20. The DNA sensor includes: a substrate 1; and functional molecules, that is, DNA probes 2, which are fixed onto the substrate 1. The DNA probes 2 form double strands together with complementary DNAs 3 as ligand molecules. Subject materials such as blood, saliva and river water, which have a possibility of containing a variety of DNAs 3, are exposed to the DNA probes 2, and thereafter, it is sensed whether or not the double strands are formed, whereby it can be detected whether or not the DNAs 3 of a sensing target are present in these subject materials.

As an analysis method, for example, there is a method of detecting a double strand forming region of the DNA probes 2 and the complementary DNAs 3 in such a manner that the varieties of DNAs 3 to be exposed are marked in advance with a fluorescent substance 4, and each of the DNAs 3 is reacted with each of the above DNA probes 2, and thereafter, fluorescence of this reaction region is measured.

Examples resembling the DNA sensors as described above are disclosed in Japanese Patent Laid-open Publication No. H4-505763 and Japanese Patent Laid-Open Publication No. 2007-285927.

Another example regarding a sequencer that measures a sequence (base sequence of a nucleic acid such as DNA is disclosed in Japanese Patent Laid-open Publication No. 2002-525125.

SUMMARY OF THE INVENTION

In the conventional sensor, sensitivity thereof has sometimes been lowered. The reason for this is because a formation density of the functional molecules has been low. Specifically, heretofore, it has been difficult to fix a sufficient amount of the functional molecules (DNA probes 2) to a predetermined region, and hence, an amount of signals emitted by a combination of the functional molecules 2 and the ligand molecules (DNAs 3) has also been small. As a result, an amount of the signals sensed by the sensor has also been reduced, and the sensitivity of the sensor has been lowered.

In this connection, it is an object of the present invention to provide a sequencer that enhances sensitivity thereof.

A sensor according to the present invention includes:
a base material having a surface made of silicon:
a plurality of fibrous protrusions which are made of silicon dioxide and are directly joined to the surface of the base material made of silicon: and
a plurality of functional molecules respectively formed on the fibrous protrusions.

Moreover, a sequencer according to the present invention includes:
a base material having a surface made of silicon;
a fibrous protrusion that is made of silicon dioxide and is directly joined to the surface of the base material made of silicon,
wherein plurality of nucleic acid strands are ixed onto the fibrous protrusion, and nucleic acid sequences of the nucleic acid strands are measured.

In accordance with the sensor according to the present invention, sensitivity thereof can be enhanced. The reason for this is because functional molecules can be fixed onto a base material with a high density. Specifically, in accordance with the present invention n, a surface area of the base material is increased by the above-mentioned fibrous protrusions, and the functional molecules can be formed with a high density even in a narrow space. Hence, reaction between the respective functional molecules and the ligand molecules can be obtained sufficiently, and can be detected as a large signal. As a result, the sensitivity of the sensor can be enhanced.

Moreover, in accordance with the sequencer according to the present invention, measurement accuracy of nucleic acid sequences can be enhanced. The reason for this is because a density of the nucleic acids in a unit region can be increased. Specifically, in accordance with the present invention, a plurality of fibrous protrusions are formed on the substrate, and the nucleic acids are amplified on the fibrous protrusions. Accordingly, a surface area of a support body is increased, and an amplified amount of the nucleic acids in one region is increased. Then, as a result, a signal detectable from the whole of the nucleic acid colony is increased. As a result, the measurement accuracy of the nucleic acid sequences can be enhanced.

BRIEF DESCRIPTION CF THE DRAWINGS

The present invention will become readily understood from the following description of preferred embodiments thereof made with reference to the accompanying drawings, in which like parts are designated by like reference numeral and in which.

DETAILED DESCRIPTION OF THE PREFERRED EMBODIMENTS (First Embodiment)

In a first embodiment, a description will be made of a DNA sensor taken as an example of an embodiment of the present invention.

Figure 1:
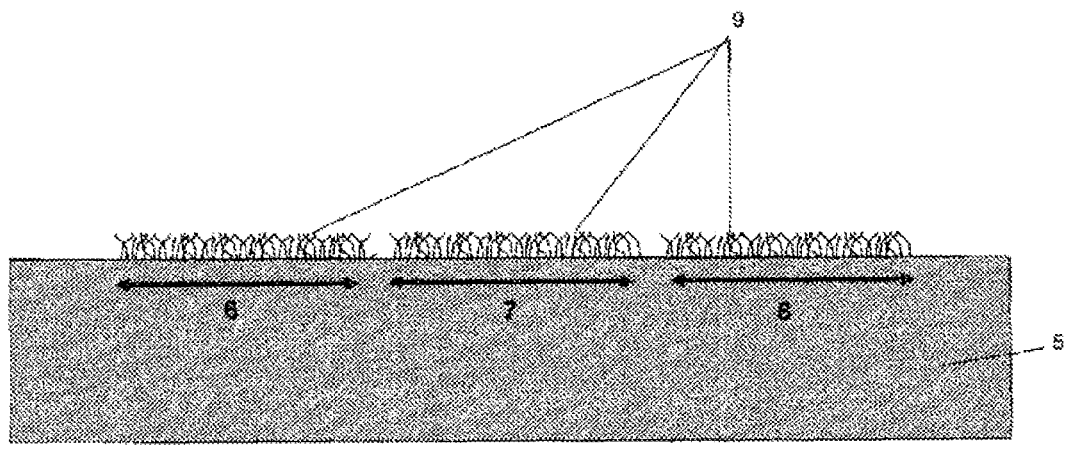
FIG. 1 is a crass-sectional view of a sensor according to a first embodiment of the present invention.
Figure 2:
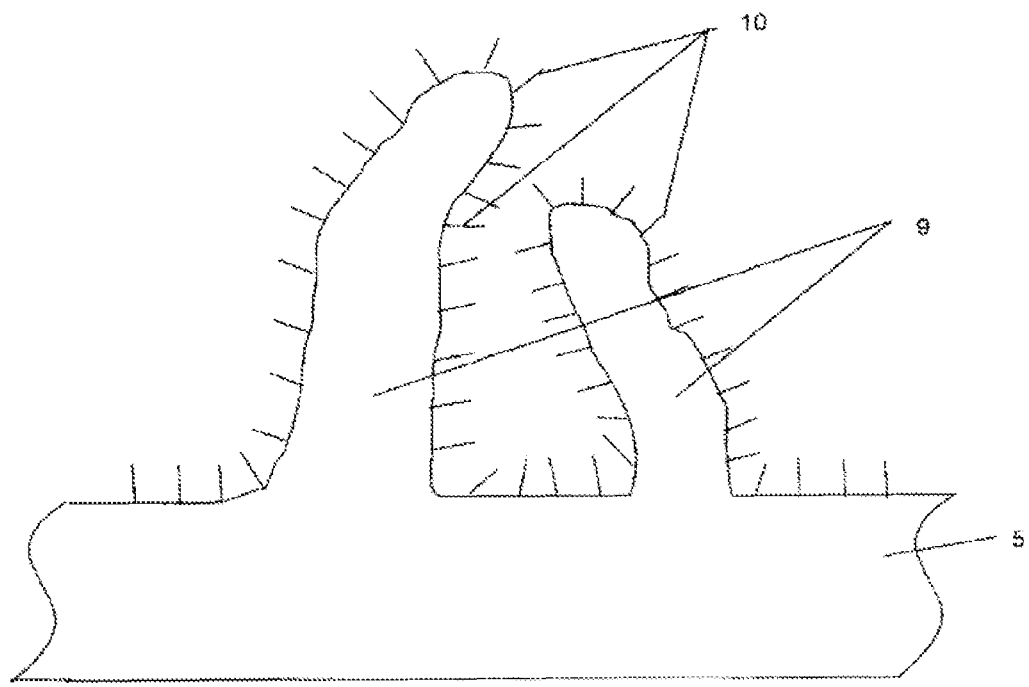
FIG. 2 is an enlarged cross-sectional view of a main portion of the sensor.

As shown in a cross-sectional view of FIG. 1, the DNA sensor has a substrate 5 made of silicon as a base material. A surface of the substrate 5 is partitioned into a plurality of regions 6 to 8, and for each of these regions 6 to 8, a plurality of fibrous protrusions 9 made of silicon dioxide, in each of which one end of the fibrous protrusion 9 is directly joined to the substrate 5, are formed. Herein, "directly joined" refers to a state where the fibrous protrusions 9 are directly formed on the substrate 5, and atoms or molecules as being components for constituting the fibrous protrusions 9, are directly bonded to the substrate 5, and generally, refers to a state where the molecules are covalently bonded to each other. In the first embodiment, silicon atoms on the surface of the substrate 5 and silicon atoms in the fibrous protrusions 9 are covalently bonded to each other through oxygen atoms in the atmosphere. Moreover, a silane coupling agent is adhered onto surfaces of these fibrous protrusions 9, whereby coating layers (not shown) in a matrix shape are formed. Moreover, in the first embodiment, linker molecules (not shown) are contained in these coating layers, and as shown in FIG. 2, a plurality of DNA probes 10 are joined by using these linker molecules as bases.

Note that, in the first embodiment, functional molecules, that is, DNA probes 10 different for each of the regions 6 to 8 on the silicon substrate 5 are joined thereto. Specifically, the DNA probes 10 are polymers in which monomers of adenine (A), guanine (G), thymine (T) and cytosine (C) are arrayed in a variety of orders, and in the first embodiment, the DNA probes 10 are formed, in which such order sequences are changed for each of the regions 6 to 8.

In the first embodiment, a silicon substrate 5 made of single crystal silicon is used as the substrate 5. However, the surface thereof just needs to be made of silicon, and the silicon may be in monocrystalline, polycrystalline, amorphous, and other states. Moreover, a so-called Silicon On Insulator (SOI) substrate may be used, for example, in which front and back surfaces are made of silicon, and a silicon dioxide layer is inserted therebetween. Moreover, as the substrate 5 of the embodiment, a substrate 5 with a thickness of approximately 400 μm is used. It is suitable that the thickness of the substrate 5 be 1 mm or less.

Moreover, in the first embodiment, an overall length of the fibrous protrusions 9 is set at 1 to 500 μm, a diameter thereof is set at 0.01 μm to 10 μm, and an interval among the plurality of fibrous protrusions 9 is set at 0.01 μm to 10 μm.

Figure 3:
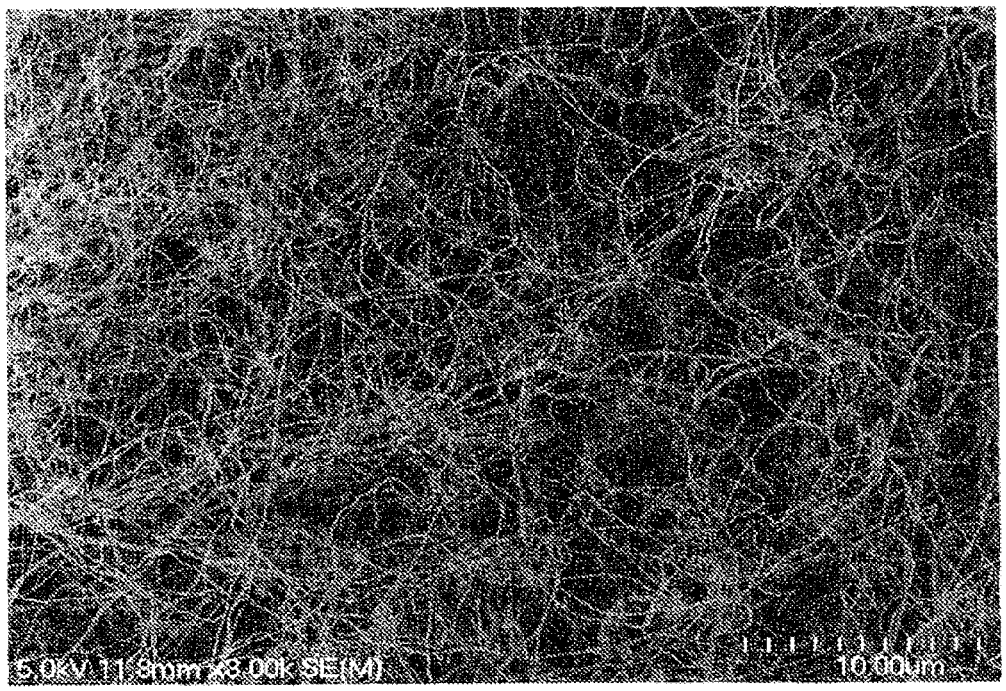
FIG. 3 is a SEM picture of fibrous protrusions of the sensor.

As shown in FIG. 3, the fibrous protrusions 9 are grown until minutely undulating and curling in order to increase a surface area thereof, each one of the fibrous protrusions 9 has a crimped shape, and the fibrous protrusions 9 are densely formed in a state of intertwining with one another. Moreover, those branched in free directions may be mixedly present in the fibrous protrusions 9. The fibrous protrusions 9 intertwine with one another, and have a plurality of such branches, whereby the fibrous protrusions 9 are robustly formed.

Figure 14:
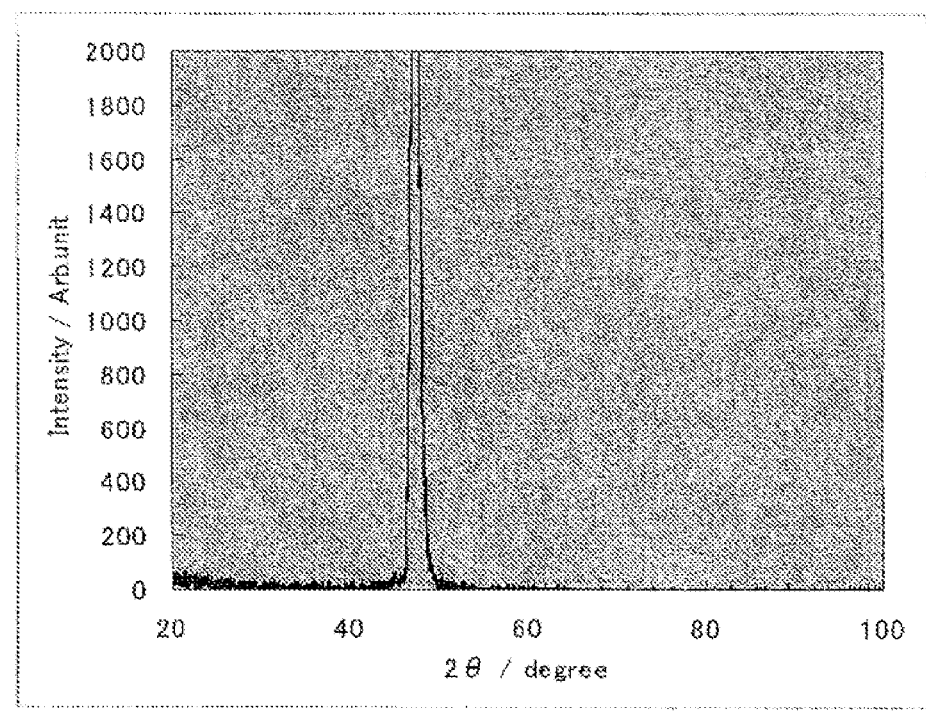
FIG. 14 is a graph showing a result of X-ray spectroscopic analysis for the fibrous protrusions in the first embodiment of the present invention.

Moreover, the fibrous protrusions 9 of the first embodiment are de of amorphous silicon dioxide, and thereby have a structure that is hard to break as compared with single crystal silicon dioxide. Note that, when a region in which the fibrous protrusions 9 are formed is measured by X-ray spectroscopic analysis, then as shown in FIG. 14, there are no large peaks except for a peak of Si (110), which is located at a region where 2θ/degree is approximately equal to 47° and it is concluded that the fibrous protrusions 9 are made of the amorphous silicon dioxide.

In the first embodiment, in order to further facilitate the bonding between the surfaces of the fibrous protrusions 9 and the DNA probes 10, the silane coupling agent containing the linker molecules adhered onto the surfaces of the fibrous protrusions 9. However, these silane coupling agent and linker molecules are not essential compositions.

Note that the silane coupling agent enhances bonding properties among the surfaces of the fibrous protrusions 9, and an agent such as poly-L-lysine, which has a composition other than that of the silane coupling agent, may be used as such an agent.

Moreover, the linker molecules serve as the bases of the DNA probes 10, and for example, there are mentioned aryl acetylene, ethylene glycol oligomer, diamine, amino acid and the like, and mixtures thereof. Note that, in some cases, the above-mentioned silane coupling agent itself becomes the linker molecules.

Next, a manufacturing method of the DNA sensor of the first embodiment will be described.

Figure 4:
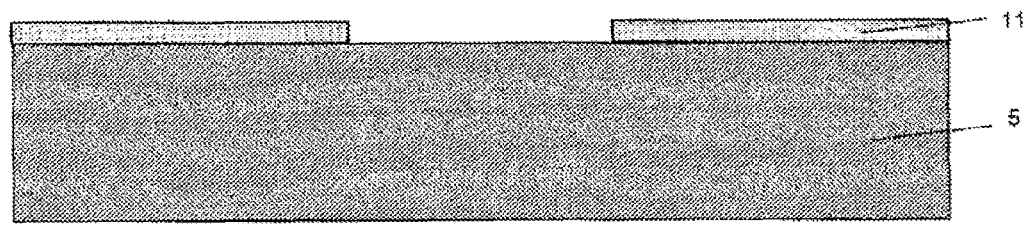
FIG. 4 is a cross-sectional view for describing a manufacturing method of the sensor.

(a) First, as shown in FIG. 4, the substrate 5 is partitioned into regions, and boundary portions among these regions are covered with a protection film 11 made of silicon dioxide, or resin of photoresist et al. In FIGS. 4 to 7, any one of the regions 6 to 8 shown in FIG. 1 is only shown.

Figure 5:
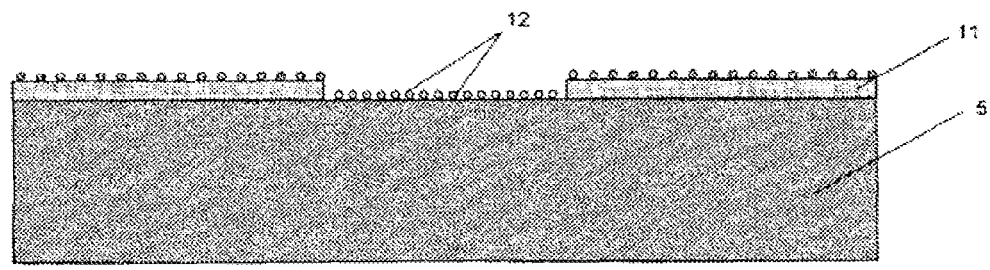
FIG. 5 is a cross sectional view for describing the manufacturing method of of the sensor.

(b) Next, when at least any one of gases of $CF_4$, $CHF_3$, $C_2F_6$, $C_3F_8$, and $C_4F_8$; is decomposed in plasma, and is introduced onto the surface of the silicon substrate 5, then as shown in FIG. 5, a seed layer 12 is formed on the surface of the substrate 5.

The seed layer 12 is a layer made of an organic polymer containing carbon element referred as C and fluorine element referred as F or C, F, and H elements, and the seed layer 12 can be formed by decomposing fluorocarbon-series gas such as the above-mentioned $CF_4$, $CHF_3$, $C_2F_6$, $C_3F_8$, and $C_4F_8$ by using a plasma CVD method.

In the case of using inductive coupled plasma (ICP) in order to decompose the above gas in the plasma, a decomposition degree of the gas is increased, and it is easy to uniformly form the seed layer 12.

Note that, in order to uniformly form the fibrous protrusions 9 in subsequent steps by the seed layer 12, the surface of the silicon substrate 5 is desirably made of pure silicon. However, the surface of the silicon substrate 5 may be in a state where an extremely thin natural oxide film is formed thereon.

Figure 6:
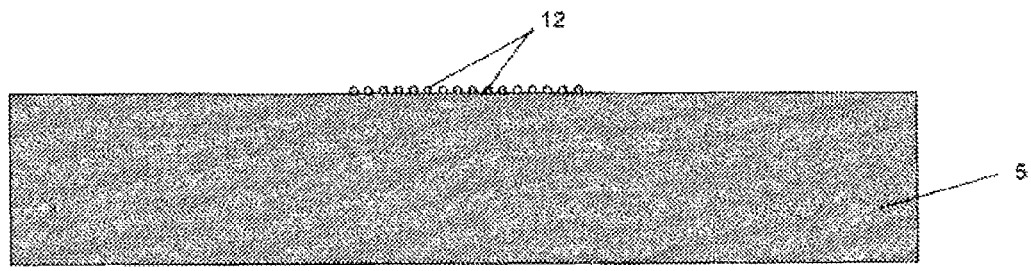
FIG. 6 is a cross-sectional view for describing the manufacturing method of the sensor.

(c) Next, as shown in FIG. 6, the protection film ii is removed by chemical treatment using a chemical agent. As in the first embodiment, the seed layer 12 formed by the plasma CVD method has a relatively strong chemical tolerance, and accordingly, only the protection film 11 can be selectively removed.

Figure 7:
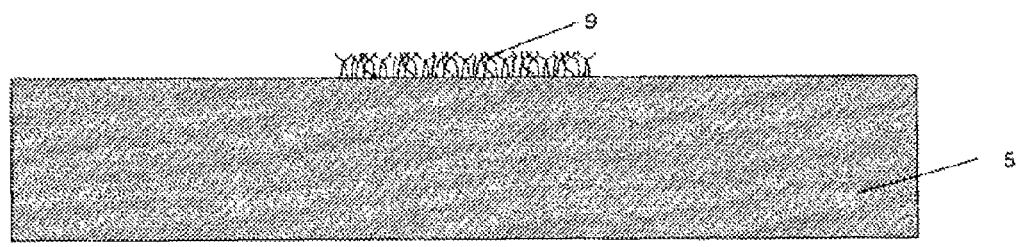
FIG. 7 is a cross-sectional view for describing the manufacturing method of the sensor.

(d) Thereafter, the substrate 5 is fired at 1000 to 1150° C. under a low-oxygen atmosphere. Then, as shown in FIG. 7, on the surface (region where the seed layer 12 of FIG. 5 is formed) of the substrate 5, the fibrous protrusions 9 made of silicon dioxide are formed. In accordance with this method, the fibrous protrusions 9 turn to a state of being directly joined to the silicon surface of the substrate 5, whereby the fibrous protrusions 9 are excellent in heat durability, and become less likely to be peeled off. Moreover, the fibrous protrusions 9 are formed in such a manner that the substrate 5 grows around the seed layer 12 taken as cores, and accordingly, other substances are less likely to be mixed thereinto, and a composition with fewer impurities is achieved.

Note that, in the firing step, the fibrous protrusions 9 are not formed on the surface of the silicon substrate 5, on which the seed layer 12 is not formed.

In the firing step, it is conceived that the seed layer 12 made of the respective atoms of C and F or the respective atoms of C, F, and H disappears by being burnt, and does not become a factor to inhibit hydrophilicity.

It is also possible to form the fibrous protrusions 9 by using a metal catalyst. In such a case, first, a metal catalyst layer is formed on the surface of the substrate 5 by evaporation, sputtering, and the like. As the metal to be used as the catalyst, Au, Fe, Ni, Co, and the like are desirable, and a thickness of the metal catalyst layer is approximately several nanometers.

Next, when the substrate 5 on which the metal catalyst layer is formed is fired at 1000 to 1150° C. under the low-oxygen atmosphere, the fibrous protrusions 9 made of silicon dioxide are formed on the surface of the substrate 5. Also in this case, the fibrous protrusions 9 turn to the state of being directly joined to the silicon surface of the substrate 5, whereby the fibrous protrusions 9 are excellent in heat durability, and become less likely to be peeled off. Moreover, the fibrous protrusions 9 are formed in such a manner that the substrate 5 grows around the seed layer 12 taken as cores, and accordingly, other substances are less likely to be mixed thereinto, and the composition with fewer impurities is achieved.

Note that the low-oxygen atmosphere is composed of an atmosphere of nitrogen, argon, or the like, or of a vacuum atmosphere.

In the case where the fibrous protrusions 9 are formed by using the metal catalyst by the above method, the metal catalyst may be supported on the fibrous protrusions 9.

Next, a method of bonding the fibrous protrusions 9 and the DNA probes (denoted by reference numeral 10 in FIG. 2) to each other will be described with reference to FIGS. 8 to 13. FIG. 8 to FIG. 13 schematically show the respective components while changing scales thereof in order to facilitate the description.

Figure 8:
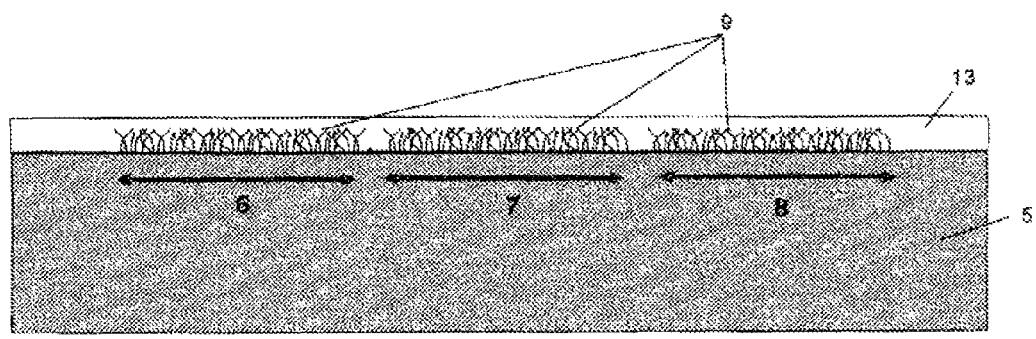
FIG. 8 is a crass-sectional view for schematically describing the manufacturing method of the sensor.
Figure 9:
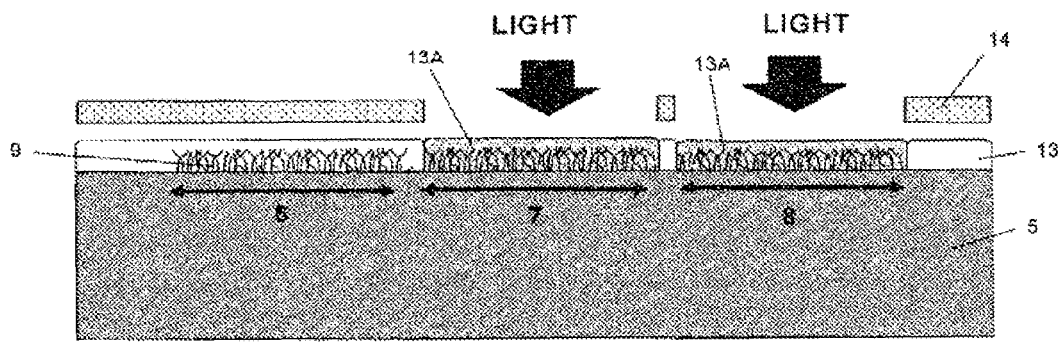
FIG. 9 is a cross-sectional view for schematically describing manufacturing method of the sensor.

(a) As shown in FIG. 8, the surface of the substrate 5 is coated with a coating layer 13 containing the silane coupling agent. To the coating layer 13, the linker molecules (not shown) in which reaction groups are modified by blocking groups are bonded. Specifically, in the first embodiment, the above-mentioned blocking groups are bonded to the surfaces of the fibrous protrusions 9 through the linker molecules and the coating layer 3. In the first embodiment, a substance capable of unblocking upon reaction with light is used as the blocking groups. Examples of the blocking groups include ortho-nitrobenzyl derivative, 6-nitroveratryl oxycarbonyl, 2-nitrobenzyl oxycarbonyl, cinnamoyl derivative, and the like. In the case where the linker molecules are not used, the blocking groups and the reaction groups of the fibrous protrusions 9 just need to be bonded to each other (b) Next, as shown in FIG. 9, the surface of the substrate 5 is masked by a mask 14 so as to expose only the regions 7 and 8 as a part among the plurality of regions 6 to 8 on the substrate 5.

(c) Subsequently, when the surface of the substrate 5 is irradiated with light from above the mask 14, the blocking groups are removed (unblocked), and the reaction groups of the linker molecules are exposed. The linker molecules in the coating layer 13A shown in FIG. 9 are in a state where the blocking groups are removed and the reaction groups are exposed. In this case, as irradiation light, light with a predetermined wavelength, which is capable of unblocking the blocking groups, is used.

Figure 10:
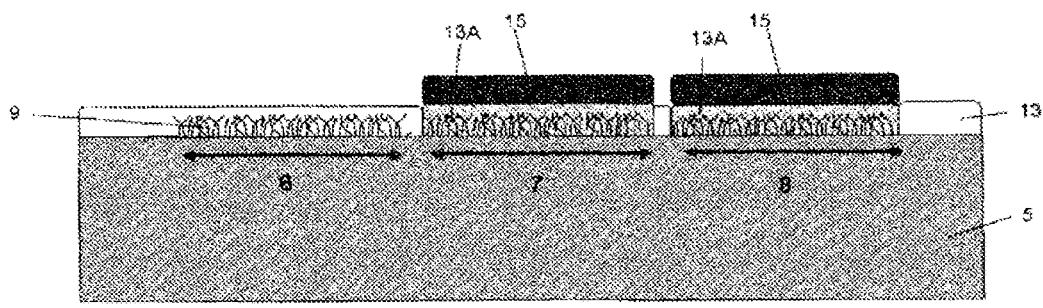
FIG. 10 is a cross-sectional view for schematically describing the manufacturing method of the sensor.

(d) Thereafter, when a solution containing a nucleotide monomer 15 of any of adenine (A), guanine (G), thymine (T), and cytosine (C) is injected onto the silicon substrate 5, then as shown in FIG. 10, the reaction groups of the exposed linker molecules and the monomer 15 are bonded to each other.

In the first embodiment, the blocking groups and the fibrous protrusions 9 are bonded to each other through the linker molecules. However, in the case where the blocking groups are directly bonded to the fibrous protrusions 9 without using the linker molecules, the monomer 15 and the reaction groups of the fibrous protrusions 9 in which the blocking groups are unblocked are bonded to each other.

Herein, in the first embodiment, a monomer modified by photoreactive blocking groups is used as the monomer 15. These blocking groups may be the same substance as the blocking groups of the linker molecules, or may be a different substance therefrom.

Figure 11:
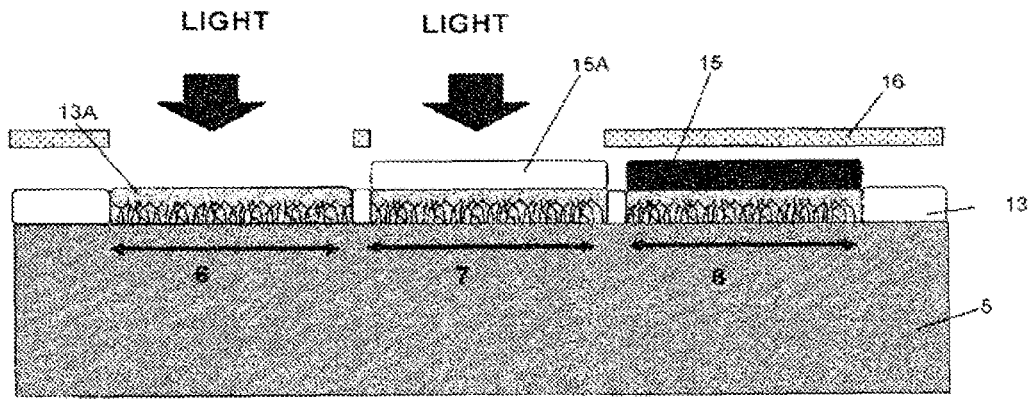
FIG. 11 is a cross-sectional view for schematically describing the manufacturing method of the sensor.
Figure 12:
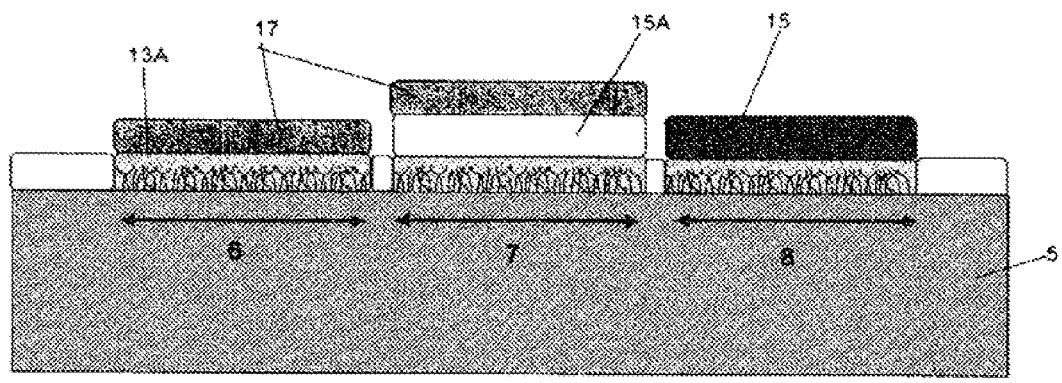
FIG. 12 is a cross-sectional view for schematically describing the manufacturing method of the sensor.

Next, as shown in FIG. 11, the surface of the substrate 5 is masked by another mask 16, whereby only such partial regions 6 and 7 are exposed. The regions 6 and 7 thus exposed may be the same region as the region to which the monomer 15 is bonded in the previous step. Then, the regions 6 and 7 are irradiated with light with a predetermined wavelength, whereby the blocking groups in the monomer on the region 7 and in the linker molecules of the coating layer on the region 6 are respectively unblocked. FIG. 11 shows the coating layer 13A and the monomer 15A, from which the blocking groups are unblocked (f) Then, as shown in FIG. 12, in the same manner as in the step of fixing the monomer 15 described above, a solution of a monomer 17 modified by the blocking groups is injected, and the monomer 15A in which the blocking groups on the region 7 are unblocked and the linker molecules in which the blocking groups on the region 6 are unblocked are bonded to each other.

As described above, when the step of bonding four types of the nucleotide monomers to one another by using different masks is repeated, the DNA probes 10 different in type can be formed for each of the regions 6 to 8.

Figure 13A:
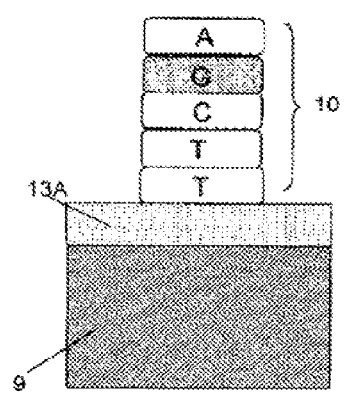
FIGS. 13A to 13C are cross-sectional views schematically showing a main portion of the sensor.
Figure 13B:
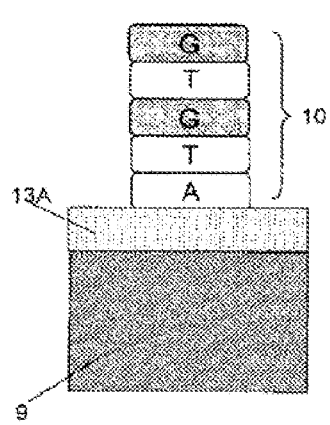
Figure 13C:
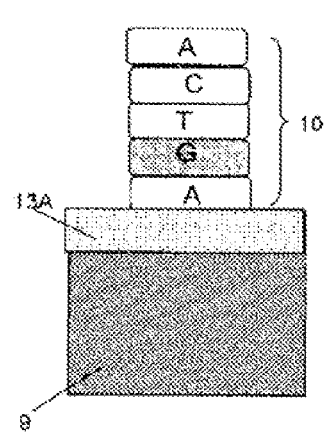

FIG. 13A, FIG. 13B, and FIG. 13C schematically show the DNA probes 10, which are formed on the surfaces of the fibrous protrusions 9 on the region 6, the region 7, and the region 8, respectively. The number of nucleotide monomers which form each of the DNA probes 10 is not particularly limited; however, approximately 10 to 30 (length: approximately 0.003 to 0.01 μm) is suitable for forming the double strand. Moreover, by a combination of the masks, DNA probes 10 having various types of sequences can also be formed quickly.

Moreover, in the first embodiment, the photoreactive blocking groups are used as the blocking groups; however, for example, substances capable of unblocking by a current, an electrolyte, an ion beam, and the like may be used. In this case, in the step of unblocking the blocking groups, the current, the electrolyte, and the on beam just need to be individually applied.

In the first embodiment, the method of polymerizing the monomer by controlling the reaction regions by using the blocking groups as mentioned above is used. However, for example, a method of stacking the monomers on a predetermined region by using a photolithography technology may also be used.

Moreover, in the first embodiment, as an example of a method of selectively forming the fibrous protrusions 9 on the predetermined regions 6 to 8 of the substrate 5, there is mentioned the method of forming the protection film (denoted by reference numeral 11 in FIG. 4) in advance on the surface of the substrate; however, other methods may be selected. For example, there may be selected such a method, in which the fibrous protrusions 9 are first formed on the whole of the region on the silicon substrate 5, the regions 6 to 8 on which the fibrous protrusions 9 are desired to be left are thereafter covered with the protection film made of the resin or the like, the fibrous protrusions 9 on the regions from which the fibrous protrusions 9 are desired to be removed are removed by etching by using a usual chemical agent such as HF and BHF, and the protection film is thereafter removed. In this case, the above-mentioned thermal oxide film is not formed on the exposed surface.

As a method of removing the protection film, it is desirable to remove the protection film by chemical treatment using a solvent and the like. This is because, in the case of using the chemical treatment, the minute fibrous protrusions 9 are less likely to be broken as compared with mechanical treatment.

For example, the DNA sensor formed as described above has double strands from the DNAs marked in advance with a fluorescent substance or the like and from the DNA probes 10, or the DNA sensor has a fluorescent substance inserted into the formed double strands. Thus, the DNA sensor can measure by means of light whether or not the double strands are formed. Besides, it can be measured whether or not the double strands are formed based on detecting a change of the current or voltage, surface roughness, and the like as well as the light.

A description will be made below of effects in the first embodiment.

In the first embodiment, sensitivity of the sensor can be enhanced. The reason for this is because the DNA probes 10 as the functional molecules can be formed with a high density, Specifically, in the present invention, a surface area of the substrate 5 is increased by the fibrous protrusions 9, and receptors can be formed with a high density even in a narrow space. Hence, the reaction between the respective DNA probes 10 and complementary DNAs (ligand molecules) can be obtained sufficiently, and can be detected as a large signal. Then, as a result, the sensitivity of the sensor can be enhanced.

Moreover, in the first embodiment, since the fibrous protrusions 9 are made of silicon dioxide, the surfaces thereof are hydroxylated more as compared with the surface of the substrate 5. Hence, bonding properties between the fibrous protrusions 9 and a chemical substance such as the linker molecules are enhanced, and the DNA probes 10 can be fixed with a higher density.

Moreover, as compared with the exposed surface (surface on which the fibrous protrusions 9 are not formed) of the substrate 5, the region where the fibrous protrusions 9 are formed has high hydrophilicity and water retention properties. Hence, in the case of supplying a polar solvent onto the substrate 5, an occurrence of bubbles can be suppressed in the region where the DNA probes 10 are formed since the polar solvent has high affinity with the fibrous protrusions 9. Specifically, in the first embodiment, the bubbles are less likely to be generated, for example, in the step of injecting the monomer solution onto the substrate 5 or injecting a measurement liquid thereonto. Then, as a result, the DNA probes 10 can be formed with a higher density, or the measurement can be performed with high accuracy. Note that, at least one of the hydrophilicity and the water retention properties contributes to reduction of she bubbles.

Moreover, in the first embodiment, the DNA probes 10 are formed on the fibrous protrusions 9, and accordingly, in the region where the DNA probes 10 are fixed, reflectivity thereof is lowered as compared with the flat surface. Hence, for example, in the case of performing the fluorescence analysis, excitation light generated in the case of irradiating silicon atoms with light is mixed with reflected light from the substrate 5, and sometimes becomes a factor of noise at the time of the fluorescence detection. However, in the present invention, the above-described excitation light can be reduced by being shaded by the fibrous protrusions 9, and a cordingly, the noise can be reduced as a result.

(Second Embodiment)

Figure 15:
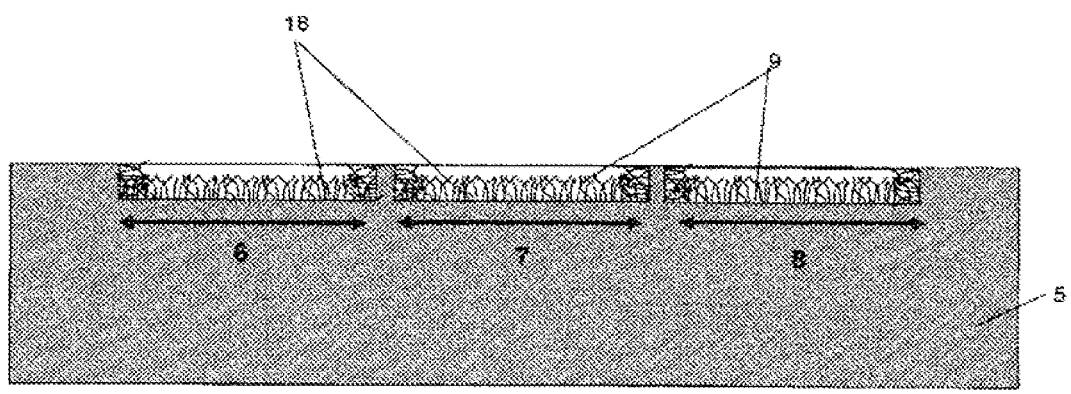
FIG. 15 is a cross-sectional view of a sensor according to a second embodiment of the present invention.

A main difference between the second embodiment and the first embodiment is a shape of the substrate 5 as shown in FIG. 15. Specifically, in the second embodiment, recessed portions 18 are formed in advance on the surface of the substrate 5 by wet etching or dry etching, and on bottom surfaces of the recessed portions 18, the fibrous protrusions 9 are formed. In such a way, in the second embodiment, the fibrous protrusions 9 on the respective regions 6 to 8 can be suppressed from growing beyond the respective regions 6 to 8. Specifically, a growing direction of the fibrous protrusions 9 is suppressed by suppressing surface diffusion thereof. Hence, shape accuracy of the regions where the fibrous protrusions 9 are formed can be enhanced.

Moreover, in the second embodiment, for example, in the step of injecting the monomer solution onto the substrate 5 or infecting the measurement liquid thereonto, the diffusion of the monomer solution or the measurement liquid can be prevented. Hence, the inspection sensitivity of the sensor is enhanced.

In the second embodiment, the fibrous protrusions 9 are formed on the bottom surfaces and side wall surfaces of the recessed portions 18; however, the fibrous protrusions 9 may be formed only on the bottom surfaces of the recessed portions 18, or only on the sidewall surfaces thereof.

A dent depth of the recessed portions 18 is preferably made deeper than a thickness of layers where the fibrous protrusions 9 are formed, since it then becomes easy to suppress the diffusion. More preferably, the dent depth of the recessed portions 18 is made deeper, by several ten micrometers or more, than the thickness of the layers where the fibrous protrusions 9 are formed. Note that ranges of the recessed portions 18 can be appropriately selected in response to the purpose.

Descriptions of other configurations and effects, which are similar to those of the first embodiment, will not be given.

In the second embodiment, the DNA sensor is taken as an example of the sensor, and the DNA probes are taken as an example of the functional molecules; however, RNAs may be used as the functional molecules. Similarly to the DNAs, the RNAs can also be formed on the predetermined regions easily by using the blocking groups.

(Third Embodiment)

In the third embodiment, a sequencer for measuring a sequence (base sequence) of nucleic acids such as DNAs is described as follows.

Figure 16:
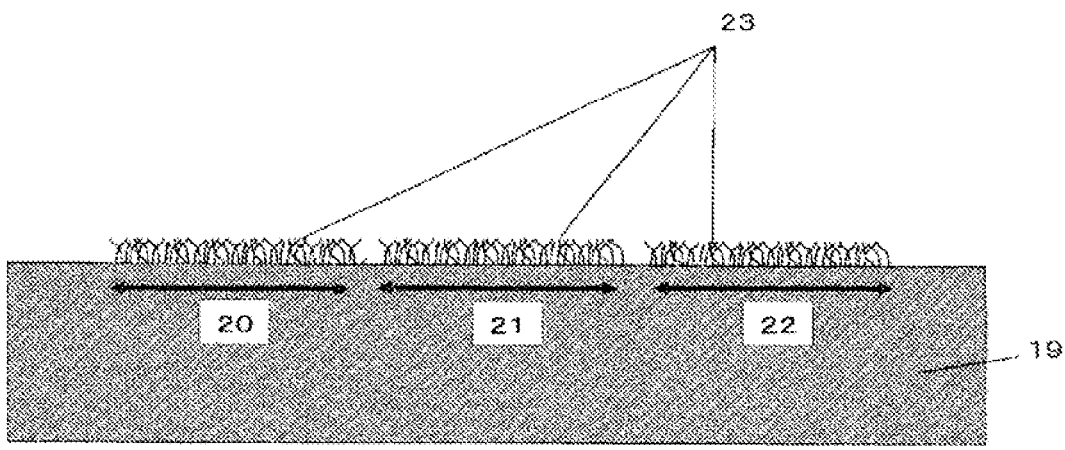
FIG. 16 is a cross-sectional view of a sequencer according to a third embodiment of the present invention.

As shown in FIG. 16, similarly to the DNA sensor of the first embodiment, the sequencer of the third embodiment also includes: a substrate 19 as a base material; and a plurality of fibrous protrusions 23 selectively formed on regions 20 to 22 of the substrate 19. In the third embodiment, an interval (interval at root portions) between a plurality of fibrous protrusions 23 in the respective regions 20 to 22 is set at 1 to 10 µm, and a diameter of the protrusions 23 is set at 0.01 µm to 10 µm. Moreover, an overall length of the fibrous protrusions 23 is approximately 1 to 500 µm.

Similarly to the first embodiment, the fibrous protrusions 23 are grown until minutely undulating and curling in order to increase a surface area thereof more each one of the fibrous protrusions 23 has a crimped shape, and the fibrous protrusions 23 are densely formed in a state of intertwining with one another. Moreover, those protrusions branched in free directions may be mixedly present in the fibrous protrusions 23. In such a way, a structure is obtained, in which a stress load is likely to be dispersed also against an external pressure, and mechanical strength is strong.

Moreover, similarly to the first embodiment, the fibrous protrusions 23 of the third embodiment are made of amorphous silicon dioxide, and have a structure less likely to be broken as compared with single crystal silicon dioxide.

A manufacturing method of the fibrous protrusions 23 as described above is similar to that of the DNA sensor shown in the first embodiment. First, on the substrate 19, fluorocarbon-series gas is decomposed in plasma by using the plasma CVD method, and a seed layer made of an organic polymer containing C and F elements or C, F, and H elements is formed. The seed layer can be formed by being fired at 1000 to 1150° C. under a low-oxygen atmosphere. It is also possible to form the fibrous protrusions 23 by using a metal catalyst. Details of the manufacturing method are similar to those of the first embodiment, and accordingly, a description thereof will not be given.

Next, a nucleic acid amplification method using the sequencer of the third embodiment is described as follows.

Figure 17A:
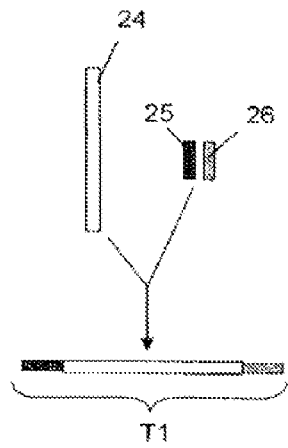
FIGS. 17A to 17F are views showing a process of amplifying nucleic acids by using the sequencer according to the third embodiment.

(a) First, DNA or RNA (hereinafter, referred to as nucleic acid) for which the nucleic acid sequence (base sequence) is desired to be measured is randomly split by using enzymes such as EcoRI and HhaI, and a nucleic acid fragment shown in FIG. 17A is formed. Although depending on reading accuracy in the sequence reading step to be described later, a length of the nucleic acid fragment 24 is usually a length of 10 to 4000 base pairs. The nucleic acid fragment 24 may have either form of a single strand or a double strand.

(b) Next, an adapter 25 containing an oligonucleotide sequence Y1 is bonded to one end of this nucleic acid fragment 24, and an adapter 26 containing an oligonucleotide sequence Z1 is bonded to the other end of the nucleic acid fragment 24. Thus, a nucleic acid template T1 as shown in FIG. 17A is formed. Note that the oligonucleotide sequence refers to a sequence of a short nucleotide sequence made of some base pairs, and contains, as constituents, bases of adenine (A), guanine (C), cytosine (C), and thymine (T) or uracil (U).

It is preferable that each of the oligonucleotide sequence Y1 and the oligonucleotide sequence Z1 be formed of approximately 5 to 100 nucleotides. In the third embodiment, the oligonucleotide sequences Y1 and Z1 are bonded to the most terminal ends of the nucleic acid template T1. However, a vicinity of the terminal end (preferably, within a range from 0 to 100 nucleotides from a terminal end 5' or terminal end 3' of the nucleic acid template T1) can be bonded to a support body 1.

(c) Moreover, in the third embodiment, a plurality of colony primers X1 and X2 are prepared. The colony primer X1 has a sequence capable of being hybridized with the oligonucleotide sequence Z1, and the colony primer X2 has a sequence capable of being hybridized with an oligonucleotide sequence (Z2 to be described later) of a nucleic acid template (T2 to be described later) formed by extension of the colony primer X1. Specifically, the colony primer X2 has a sequence corresponding to the oligonucleotide sequence Y1

(d) Next, in the third embodiment, OH groups of the fibrous protrusion 23 of the support body 1 are induced by amino-propyltriethoxysilane (ATS) and the like, and a surface of the fibrous protrusion 23 is functionalized by a difunctional coupling agent.

Figure 17B:
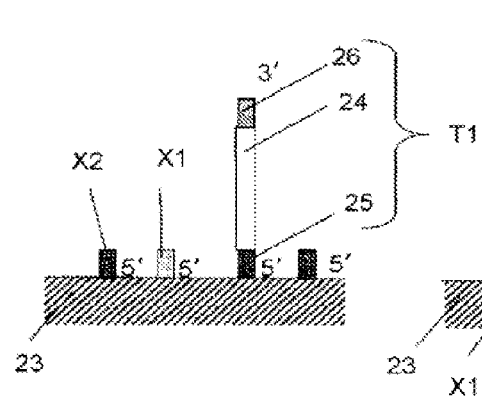

(e) Then, a solution containing the colony primers X1 and X2 and the nucleic acid template T1 is provided to the functionalized surface of the fibrous protrusion 23, and as shown in FIG. 17B, the respective terminals ends 5' of the colony primers X1 and X2 and the nucleic acid template T1 are covalently bonded to the surface of the fibrous protrusion 23. Note that, a diagonally shaded portion of FIG. 17B indicates the fibrous protrusion 23. In the third embodiment, the colony primers X1, X2, and the nucleic acid template T1 are bonded to the surface of the fibrous protrusion 23 by amide bond; however, as other bonds, covalent bonds such as ester bond and thiol bond may also be selected as above-mentioned.

Figure 17C:
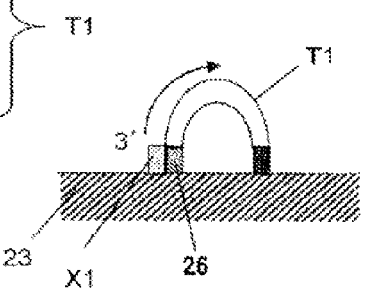

(f) Next, as shown in FIG. 17C, the nucleic acid template T1 and the colony primer X1, which are bonded to the fibrous protrusion 23, are induced, and the oligonucleotide sequence Z1 (adapter 26) of the nucleic acid template T1 and the colony primer X1 are hybridized with each other. Inducing conditions at this time may include, for example, putting such hybridization targets at a temperature of approximately 65° C.

Figure 17D:
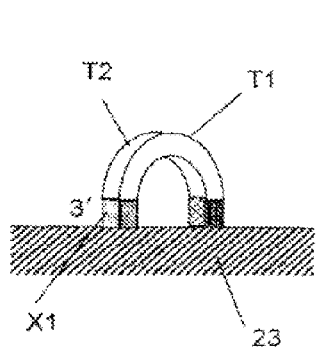

(g) Thereafter, as shown in FIG. 17D, under an appropriate temperature condition and the presence of nucleic acid polymerase (for example, DNA-dependent DNA polymerase, reverse transcriptase molecules, RNA polymerase, or the like), the nucleic acid is synthesized while using, as base substrates, four types of nucleotide precursors, that is, four types of deoxynucleoside triphosphate, which are: deoxyadenosine triphosphate (hereinafter, abbreviated as dATP); deoxyguanosine triphosphate (hereinafter, abbreviated as dGTP); deoxycytidine triphosphate (hereinafter, abbreviated as dCTP); and deoxythymidine triphosphate (hereinafter, abbreviated as dTTP).

(h) As described above, the nucleic acid polymerase extends the colony primer X1 from the terminal end 3' thereof by using the nucleic acid template T1 as a template. Then, after such extension of the primer is completed, a second nucleic acid strand complementary to the first nucleic acid template T1, that is, a nucleic acid template T2 is created.

Figure 17E:
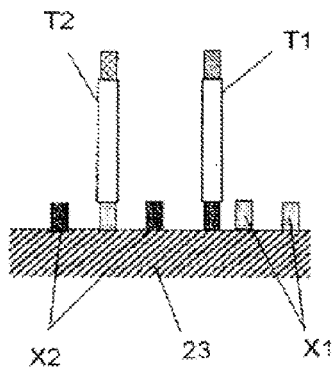

(i) Thereafter, for example by heating, a state as shown in FIG. 17E is brought, where two separate nucleic add strands (nucleic acid templates T1 and T2) are immobilized on the fibrous protrusion 23.

Figure 17F:
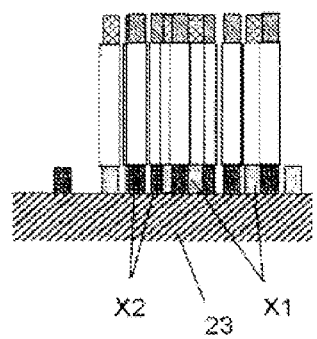

(j) Then, as shown in FIG. 17F, both of the nucleic acid template T1 first immobilized and the nucleic acid strand (nucleic acid template T2) formed by extending the colony primer X1 function as the nucleic acid templates. Specifically, the nucleic add template T1 and the nucleic acid temperature T2 are hybridized with another immobilized colony primer X1 or colony primer X2 to thereby cause the primer extension individually. Then, the nucleic acid is separated to thereby amplify the nucleic acid strands immobilized to the fibrous protrusion 23. The nucleic acid strands are amplified as described above, whereby a nucleic acid colony is created. Note that, in the third embodiment, the nucleic acid colony includes the one having the sequence corresponding to the first nucleic acid template T1, and the one having the sequence complementary to the nucleic acid template T1 (that is, corresponding to the nucleic acid template T2).

As described above, even in the other regions on the support body 1, the nucleic acid colony composed of two types of nucleic acid strands can be formed in a similar way by using, as the templates, the nucleic adds split randomly. This nucleic acid colony contributes more to the miniaturization by being formed at a small interval of less than 10 µm.

Next, the nucleic acid sequence can be measured after the nucleic acid is amplified.

In the third embodiment, among the two types of nucleic acid strands which compose the nucleic acid colony, the measurement is performed for the sequence of the nucleic acid template T1. At this time, for example, the nucleic acid strand complementary to the nucleic acid template T1 just needs to be cut off from the fibrous protrusion 23. Specifically, since the nucleic acid template T2 is bonded to the fibrous protrusion 23 through the colony primer X1, the colony primer X1 can be cut off from the fibrous protrusion 23 by a restriction enzyme. Accordingly, as shown in FIG. 18A, a nucleic acid colony made only of the nucleic acid strands corresponding to the nucleic acid template T1 can be formed.

Next, a solution containing: a primer 27 capable of being hybridized with the oligonucleotide sequence Z1 on the terminal end 3' side of the nucleic acid template T1; four types of the modified nucleotide precursors (A, T, C, and G shown in FIG. 18A); and the nucleic acid polymerase is flown on the fibrous protrusion 23. At this time, the four types of nucleotide precursors are modified in advance by a variety of fluorescent substances so as to emit mutually different types of excitation light. Then, at the moment when the nucleotide precursors are hybridized, the fluorescent substances are excited by a laser beam, and emit a fluorescent color. At this time, in one nucleic acid colony, one type among the four types of nucleotide precursors is bonded, and accordingly, color emissions with the respective wavelengths can be confirmed by the nucleic acid colony. Next, as shown in FIG. 18B, the four types of nucleotide precursors and the enzymes are flown again onto the fibrous protrusion 23, whereby the next nucleotide precursors are extended from the primer 27, are hybridized with the nucleic acid template T1, and emit colors with unique wavelengths.

As described above, in the process where the primer 27 is extended, and the nucleic acid sequence complementary to the nucleic acid templates T1 is formed from the terminal end 3' side, the color emissions occur in a variety of orders depending on the nucleotide sequence of the nucleic acid template T1. Hence, the color emissions are recorded, whereby the nucleotide sequence of the nucleic acid templates can be read for each nucleic acid colony, and a sequence of the respective diffused fragments is revealed.

Figure 18A:
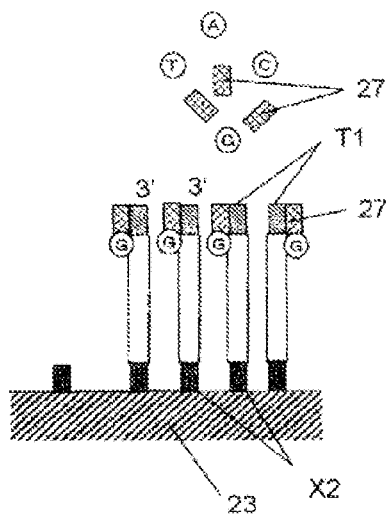
FIGS. 18A and 18B are views showing a process of measuring sequences of the nucleic acids by using the sequencer according to the third embodiment.
Figure 18B:
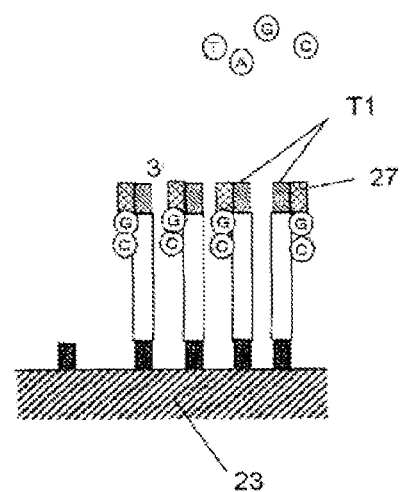

In FIG. 18A described above, if the nucleotide precursors are chemically modified in advance so that an extension reaction cannot occur subsequently to an occurrence of one hybridization reaction, then one nucleotide sequence on the single can be reliably determined. Specifically, a chemical modification substance is removed afterward, and the chemically modified nucleotide precursors are flown again, whereby the reactions can be reliably determined one by one.

Here, with regard to the nucleic acid template, if a large number of the nucleic acids for which the sequences are desired to be measured are prepared in advance, and are formed by being split randomly, then not only the sequence of the nucleic acid fragments but also the sequence of the original nucleic acids can be analyzed. In the third embodiment, the support body 1 is partitioned in the plurality of regions, the fibrous protrusions 23 are formed selectively in the regions thus partitioned, and the nucleic acid colony is formed for each of the regions. Hence, as shown in Table 1, the sequences read from the nucleic acid colonies in the respective regions are compared with one another, and if there are the same sequence portions, then the portions concerned are arrayed so as to superpose on each other, whereby the entire sequence of the original nucleic acids can be read gradually.

TABLE 1

| Measurement Region | Read Sequence |
|---|---|
| Region 3 | AATCGCTATTTACCCGG |
| Region 4 | TTTACCCGGATTCGCCC |
| Region 5 | GAATCGC |

A description will be made below of effects in the third embodiment.

In the third embodiment, a density of the nucleic acids in the unit region is increased, and measurement accuracy of the nucleic acid sequence can be enhanced. The reason for this is because the plurality of fibrous protrusions 23 are formed on the substrate 19, and the nucleic acids are amplified on the fibrous protrusions 23. In such a manner, in the third embodiment, the surface area of the support body 1 is increased, and an amplified amount of the nucleic acids in one region is increased. Then, as a result, the signal detectable from the whole of the nucleic acid colony is increased, and the measurement accuracy of the nucleic acid sequence can be enhanced.

Moreover, in the third embodiment; since the fibrous protrusions 23 are made of silicon dioxide, the surfaces thereof are hydroxylated more as compared with the surface of the substrate 19. Hence, bonding properties between the fibrous protrusions 23 and the chemical substance for bonding the nucleic acid templates and the colony primers are enhanced, and the nucleic acid templates and the colony primers can be fixed with a higher density.

Moreover, as shown in FIG. 16, the regions 20 to 22 where the fibrous protrusions 23 are formed have high hydrophilicity as compared with the exposed surface (surface on which the fibrous protrusions 23 are not formed) of the substrate 19. Hence, in the case of supplying a polar solvent onto the substrate 19, an occurrence of bubbles can be suppressed in the region where the nucleic acid templates T1 and the colony primers X1 and X2 are formed since the polar solvent has high affinity with the fibrous protrusions 23. Hence, the measurement can also be formed with high accuracy.

Furthermore, in the third embodiment, the nucleic acid templates T1 are formed on the fibrous protrusions 23, and accordingly, in the region where the nucleic acid templates T1 are fixed, reflectivity thereof is lowered as compared with the flat surface. Hence, for example, in the case of performing the analysis by fluorescence, excitation light generated in the case of irradiating silicon atoms with light is mixed with reflected light from the substrate 19, and sometimes becomes a factor of noise at the time of the fluorescence detection. However, in the present invention, the above-described excitation light can be reduced by being shaded by the fibrous protrusions 23, and accordingly, the noise can be reduced as a result.

In the third embodiment, the plurality of fibrous protrusions 23 are formed on each of the regions 20 to 22; however, one fibrous protrusion 23 may be formed on each of the regions 20 to 22. Also in this case, the surface area of the substrate 19 is increased, and the nucleic acids can be amplified more.

Moreover, in the third embodiment, the immobilized nucleic acids are amplified on the fibrous protrusions 23 by using the nucleic acid templates T1 as templates; however, other fixing methods of the nucleic acid strands may be adopted. For example, nucleic acids amplified in advance may be flown on the fibrous protrusions 23, and the nucleic acids may be fixed by being individually bonded thereto. As described above, the sequencer of the third embodiment, which has the fibrous protrusions 23, is used for fixing the variety of nucleic acids. Then, in each of such sequencers according to the respective modes, the surface of the substrate 19 is increased by the fibrous protrusions 23, and accordingly, the number of nucleic acids which can be fixed in the unit region is increased, and the measurable signal is also increased. Hence, the measurement accuracy of the nucleic acid sequence can be enhanced.

Furthermore, in the third embodiment, as an example of the measurement method of the nucleic acid sequence, there is mentioned the method of analyzing the fluorescence by the hybridization between the fixed nucleic acid strands (nucleic acid templates) and the nucleotide precursors. However, this measurement method is merely an example, and a variety of methods can be used. For example, there is also a method of measuring the sequence by capturing, as a change of light or an electric signal, a state of an electromagnetic field changed by the hybridization reaction between the fixed nucleic acid strands and the nucleotide precursors.

(Fourth Embodiment)

Figure 19:
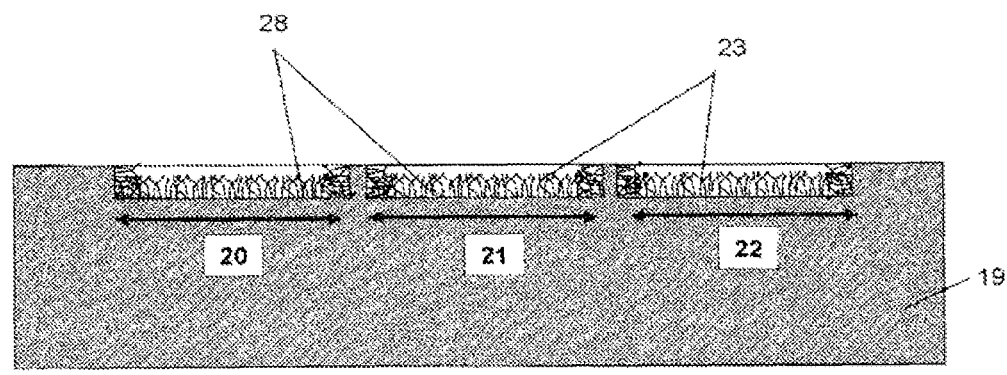
FIG. 19 is a cross-sectional view of a sequencer according to a fourth embodiment of the present invention.
Figure 20:
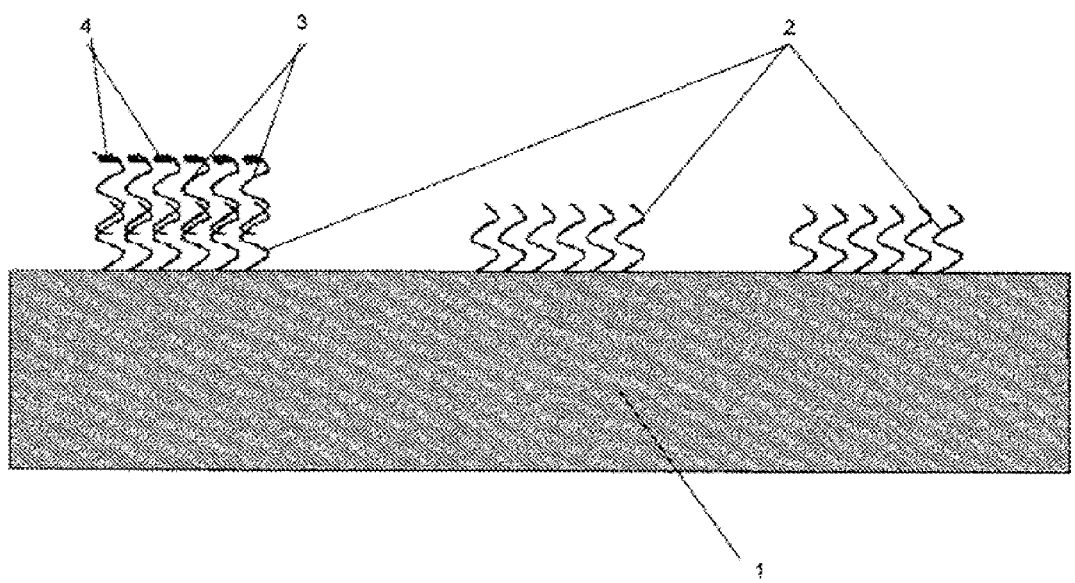
FIG. 20 is a cross-sectional view of a conventional DNA sensor.

A main difference between the fourth embodiment and the third embodiment is a shape of the substrate 19 as shown in FIG. 19. Specifically, in the fourth embodiment, recessed portions 28 are formed in advance on the surface of the substrate 19 by wet etching or dry etching, and on bottom surfaces of the recessed portions 28, the fibrous protrusions 23 are formed. Accordingly, in the fourth embodiment, the fibrous protrusions 23 on the respective regions 20 to 22 can be suppressed from growing beyond the regions 20 to 22. Specifically, a growing direction of the fibrous protrusions 23 is suppressed by suppressing surface diffusion thereof. Hence, shape accuracy of the regions where the fibrous protrusions 23 are formed can be enhanced. Hence, each nucleic acid colony can be formed for each of the regions 20 to 22, and the signal can be measured with high accuracy. Moreover, in the fourth embodiment, for example, in the step of injecting the monomer solution onto the substrate 5 or injecting the measurement liquid thereonto, diffusion of the monomer solution or the measurement liquid can be prevented. Hence, the inspection sensitivity of the sensor is enhanced.

In the fourth embodiment, the fibrous protrusions 23 are formed on the bottom surfaces and side wall surfaces of the recessed portions 28; however, the fibrous protrusions 23 may be formed only on the bottom surfaces of the recessed portions 28, or only on the sidewall surfaces thereof.

Note that a dent depth of the recessed portions 18 is preferably made deeper than a thickness of layers where the fibrous protrusions 9 are formed since it becomes easy to suppress the diffusion. More preferably, the dent depth of the recessed portions 18 is made deeper, by several ten micrometers or more, than the thickness of the layers where the fibrous protrusions 9 are formed. Further, ranges of the recessed portions 18 can be appropriately selected in response to the purpose.

Descriptions of other configurations and effects, which are similar to those of the first embodiment, will not be given, Description of other configurations and effects, which are similar to those of the third embodiment, will not be given.

In each of the first to fourth embodiments, the flat substrate is used as the base material; however, base materials with various shapes, for example, such as a spherical shape and a cubic shape, may be used.

A sensor according to the present invention can be used as a DNA sensor. Moreover, besides the DNA sensor, the sensor according to the present invention can be used as a variety of sensors such as a protein sensor, a sugar sensor, and an antigen-antibody sensor. As the variety of sensors for use, there are; a sensor that bonds, to surfaces of fibrous protrusions, a receptor and a reactive substance, which are capable of individually capturing ligand molecules desired to be detected, and measures the bonding of the receptor and the reactive substance to the ligand molecules; and a sensor that bonds, to the surfaces of the fibrous protrusions, ligand molecules desired to be measured as functional molecules, and reacts the ligand molecules with these receptor and reactive substance. If the functional molecules are polymers, monomers can be polymerized in a predetermined region by using blocking groups. Moreover, in a sequencer of the present invention, a sequence of nucleic acids such as DNAs can be measured with high accuracy.

The invention claimed is:

1. A sensor comprising:
   a base material having a surface; and
   fibrous protrusions formed from amorphous silicon dioxide and the fibrous protrusions being undulating and curling, having a crimped shape, and being configured so as to intertwine with other fibrous protrusions,
   wherein each fibrous protrusion of the fibrous protrusions has functional molecules formed respectively thereon.

2. The sensor according to claim 1, wherein the base material is formed from silicon, and
   the fibrous protrusions are directly joined to the surface of the base material.

3. The sensor according to claim 1, wherein a part of the surface of the base material where the fibrous protrusions are formed has a hydrophilicity and water retention properties higher than the hydrophilicity and water retention properties of another part of the surface where the fibrous protrusions are not formed.

4. The sensor according to claim 1, wherein the base material has a recessed portion with a bottom surface and a side wall surface, and the fibrous protrusions are formed on at least one of the bottom surface and the side wall surface.

5. The sensor according to claim 1, wherein each fibrous protrusion of the fibrous protrusions has a plurality of branches.

6. The sensor according to claim 1, wherein the surface of the base material is partitioned into a plurality of regions, and the fibrous protrusions are formed on each of these regions.

7. The sensor according to claim 1,
   wherein the fibrous protrusions have a plurality of branches.

* * * * *